US010386298B2

(12) United States Patent
Barritault et al.

(10) Patent No.: US 10,386,298 B2
(45) Date of Patent: Aug. 20, 2019

(54) NONDISPERSIVE INFRARED GAS DETECTION SENSOR

(71) Applicant: Commissariat à l'Energie Atomique et Aux Energies Alternatives, Paris (FR)

(72) Inventors: Pierre Barritault, Grenoble (FR); Serge Gidon, La Murette (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/437,808

(22) Filed: Feb. 21, 2017

(65) Prior Publication Data
US 2017/0241904 A1 Aug. 24, 2017

(30) Foreign Application Priority Data
Feb. 18, 2016 (FR) ...................................... 16 51324

(51) Int. Cl.
*G01J 3/42* (2006.01)
*G01N 21/03* (2006.01)
*G01N 21/61* (2006.01)
*G01N 21/3504* (2014.01)

(52) U.S. Cl.
CPC ............ *G01N 21/3504* (2013.01); *G01J 3/42* (2013.01); *G01N 21/0303* (2013.01); *G01N 21/031* (2013.01); *G01N 21/61* (2013.01); *G01N 2201/068* (2013.01); *G01N 2201/0873* (2013.01)

(58) Field of Classification Search
CPC .................................................. G01N 21/3504
See application file for complete search history.

(56) References Cited

U.S. PATENT DOCUMENTS

| 3,588,496 | A | * | 6/1971 | Snowman | ............ | G01N 21/031 |
| | | | | | | 250/343 |
| 5,453,620 | A | | 9/1995 | Wadsworth et al. | | |
| 6,538,251 | B1 | * | 3/2003 | Weckstrom | .......... | A61B 5/0836 |
| | | | | | | 250/339.06 |
| 2003/0058439 | A1 | * | 3/2003 | Martin | ................... | G01N 21/03 |
| | | | | | | 356/246 |
| 2005/0121614 | A1 | | 6/2005 | Stuttard | | |

(Continued)

FOREIGN PATENT DOCUMENTS

EP 2573546 A1 * 3/2013 ............. G01N 21/05
EP 2573546 A1 3/2013

*Primary Examiner* — David P Porta
*Assistant Examiner* — Jeremy S Valentiner
(74) *Attorney, Agent, or Firm* — Oliff PLC

(57) ABSTRACT

A sensor including an optical cavity capable of receiving the gas, and defined by first and second opposite ends and a connecting portion connecting said ends; a light source arranged to emit infrared light in the optical cavity; at least one infrared detector arranged to detect the infrared light; at least one mirror arranged in the optical cavity to guide the infrared light towards said at least one infrared detector; the sensor being remarkable in that it includes first and second reflective elements respectively extending at the first and second ends of the optical cavity, and having an infrared light reflection coefficient greater than or equal to 75% for any angle of incidence.

18 Claims, 5 Drawing Sheets

(56) References Cited

U.S. PATENT DOCUMENTS

| | | | | |
|---|---|---|---|---|
| 2006/0009707 A1* | 1/2006 | Daniels | ............... | A61B 5/083 |
| | | | | 600/532 |
| 2007/0007449 A1 | 1/2007 | Hubner et al. | | |
| 2007/0279633 A1* | 12/2007 | Yi | ............... | G01N 21/031 |
| | | | | 356/432 |
| 2008/0316489 A1* | 12/2008 | Ludwig | ............ | G01N 21/0303 |
| | | | | 356/437 |
| 2011/0031402 A1* | 2/2011 | Huttmann | ............ | G01N 21/03 |
| | | | | 250/340 |
| 2013/0334423 A1* | 12/2013 | Henderson | ......... | G01N 21/3504 |
| | | | | 250/343 |
| 2014/0078504 A1* | 3/2014 | Nicoletti | ............ | G01N 21/3504 |
| | | | | 356/437 |

* cited by examiner

NONDISPERSIVE INFRARED GAS DETECTION SENSOR

BACKGROUND

The present invention relates to a nondispersive infrared gas detection sensor. Such a sensor is conventionally called NDIR, for "NonDispersive InfraRed". More specifically, the present invention preferably aims at a compact NDIR sensor, having a low cost and a low electric power consumption.

The application preferably envisaged is the reliable detection of a gas, for example, $CO_2$, in an industrial environment, the detection conventionally being a threshold detection. Another possible application is the analysis of a gas, implying accurate, selective, and stable quantitative measurements, to obtain a compositional analysis, or even an individual detection of the $CO_2$ content of the breathed air.

Such a NDIR sensor may be integrated in a portable system such as a cell phone, a computer, a photographic camera, etc. The present invention may also apply in fixed house automation systems, the analysis of the quality of the inner and outer air, industrial detectors, etc.

STATE OF THE ART

A NDIR sensor conventionally comprises:
an optical cavity capable of receiving the gas;
a light source arranged to emit infrared light in the optical cavity;
at least one infrared detector arranged to detect the infrared light.

The operating principle of a NDIR sensor comprises measuring, with the infrared detector, the light intensity decrease when the gas to be detected is within the optical cavity. Indeed, the gas within the optical cavity absorbs infrared light at a wavelength (on a spectral band) specific to the gas to be detected. For this purpose, the infrared detector is conventionally provided with a filter capable of filtering said predetermined wavelength (or spectral band).

For example, under the assumption of a uniform distribution of the gas molecules, the Beer-Lambert law provides a formula for transmittance T of light through a gas:

$$T = e^{-\sigma Nl},$$

where:
σ is the absorption cross-section of a gas molecule,
N is the number of gas molecules per volume unit,
l is the length of interaction between the gas and the light.
As an example, for $CO_2$, interaction length l is preferably in the range from a few mm to a few tens of cm.

The NDIR sensor may comprise a plurality of infrared detectors, each being sensitive to a specific wavelength, and this, to detect a plurality of different gases. One of the infrared detectors may be sensitive to a wavelength corresponding to the absorption of no gas; such an infrared detector is used to follow the fluctuations of the light source and forms a reference path.

A great compactness is desired for the NDIR sensor. Due to the high interaction length (capable of a reaching a few tens of cm), it is not possible to use an optical cavity with a direct path between the light source and the infrared detector, including in the presence of lenses. "Cavity with a direct path" means a cavity operating with no mirrors which enable to fold the light beam.

On this regard, a known NDIR sensor of the state of the art, particularly of document US 2003/0058439 (hereafter, D1), comprises:

an optical cavity capable of receiving the gas, and defined by:
first and second opposite ends, and
a connecting portion connecting the first and second ends;
a light source arranged to emit infrared light in the optical cavity;
at least one infrared detector arranged to detect the infrared light;
an assembly of mirrors arranged in the optical cavity to guide the infrared light towards said at least one infrared detector.

It is thus known to fold the optical cavity, in the sense where an assembly of mirrors is arranged in the optical cavity to guide the infrared light towards the infrared detector along an indirect path originating from successive reflections on the mirrors. This solution enables to decrease the size of the NDIR sensor in the plane of the optical cavity, but not across the thickness thereof (here meaning the transversal dimension of the connecting portion between the first and second ends). Indeed, the thickness of the optical cavity is dictated by the thickness of the light source. For example, in D1, the light source is an incandescent filament having a 1.5-mm length.

Now, an additional decrease in the thickness of the optical cavity would result in decreasing the size of the light source, and thereby in a loss of optical efficiency. A possibility of compensation would be to increase the power of the light source, to the detriment of the electric power consumption.

The present invention thus aims at obtaining a NDIR gas detection sensor, which is both compact and with a low electric power consumption.

SUMMARY

Thus, the present invention aims at overcoming all or part of the above-mentioned disadvantages and relates, for this purpose, to a nondispersive infrared gas detection sensor, comprising:
an optical cavity capable of receiving the gas, and defined by:
first and second opposite longitudinal ends, and
a connecting portion extending transversely between the first end and the second end to connect the first and second ends;
a light source arranged to emit infrared light in the optical cavity;
at least one infrared detector arranged to detect the infrared light;
at least one mirror arranged in the optical cavity to guide the infrared light towards said at least one infrared detector;
first and second reflective elements respectively extending at the first and second ends of the optical cavity, and having an infrared light reflection coefficient greater than or equal to 75% for any angle of incidence;
the sensor being designed to arrange the light source between the first end and the second end, the light source being further directed towards the connecting portion.

Definitions

"Reflection coefficient" means the intensity reflection coefficient, for an angle of incidence in the range from 0° (normal incidence) and 90° (grazing incidence), for a given wavelength, and taking into account the arithmetically averaged "s" and "p" polarizations. The angle of incidence is the angle between the infrared light propagation direction and the normal to the first or to the second reflective element.

"Infrared" means a wavelength in the range from 0.78 µm to 12 µm.

Thus, such a NDIR sensor according to the invention enables to increase the optical efficiency of the optical cavity with respect to the state of the art. The mirror(s) enable to conjugate the light source with the infrared detector(s) in the plane of the optical cavity. Now, the inventors have surprisingly observed that it is possible to correctly image the light source on the infrared detector(s) with the additional presence of a waveguide arranged to guide the infrared light along the optical cavity thickness direction, that is, the transversal dimension of the connecting portion between the first and second ends. Such a waveguide is formed by the first and second reflective elements respectively extending at the first and second ends of the optical cavity, and having an infrared light reflection coefficient greater than or equal to 75% for any angle of incidence.

According to an embodiment, said at least one mirror is arranged in the transversal connecting portion. Thus, such a NDIR sensor according to this embodiment enables both to increase the optical efficiency of the optical cavity with respect to the state of the art, and to increase its compactness by decreasing the thickness of the cavity without increasing the power of the light source. The ingenious arrangement of the light source, of the mirror(s), and of the reflective elements extending at the ends of the optical cavity enables to conjugate the light source with the infrared detector(s) in the plane of the optical cavity, so as to guide the infrared light across the thickness of the optical cavity by doing away with the arranging of reflectors within the optical cavity.

According to an embodiment, the first and second ends and the connecting portion form a cylinder defining the optical cavity; the first and second ends forming the bases of the cylinder.

Definition

"Cylinder" means a surface defined by a straight line (called generatrix) following a curve (called directrix curve) along a fixed direction. The fixed direction defines the height of the cylinder, that is, the thickness of the optical cavity. The plane of the optical cavity corresponds to the plane of the directrix curve. The first and second ends are the bases of the cylinder and may be open or closed. In the case in point, the bases of the cylinder are preferably closed by the first and second reflective elements. The directrix curve may be open or closed. In the case in point, the directrix curve is preferably open to receive the light source and the infrared detectors. The directrix curve has an imaging function in that it is capable of correctly imaging the light source on the infrared detector(s). The cylinder is not limited to a specific shape of the directrix curve, such as a circle, an ellipse, a parabola, a hyperbola, etc.

According to an alternative embodiment, the connecting portion extends transversely between the first and second ends along a curvilinear direction.

Preferably, the curvilinear direction forms an arc of a circle, and the first and second ends and the connecting portion form a truncated torus defining the optical cavity; the torus being truncated by a plane perpendicular to the curvilinear direction. The truncated torus may comprise openings capable of receiving the light source and the infrared detectors.

According to another alternative embodiment, the first and second ends and the connecting portion form a frustum with parallel bases defining the optical cavity; the first and second ends forming said parallel bases.

The frustum may comprise openings capable of receiving the light source and the infrared detectors.

Advantageously, said reflection coefficient is greater than or equal to 80%, preferably greater than or equal to 85%, more preferably greater than or equal to 90%, for any angle of incidence.

Thus, such a reflection coefficient enables to increase the optical efficiency of the optical cavity.

Advantageously, said reflection coefficient is greater than or equal to 95%, preferably greater than or equal to 98%, for any angle of incidence smaller than 45°.

Preferably, the first and second reflective elements are planar mirrors.

According to a characteristic, the first and second reflective elements each comprise a reflective surface having said reflection coefficient.

Advantageously, the reflection surface is made of a metallic material, preferably selected from the group comprising gold, silver, and aluminum.

Thus, such metallic materials provide very high infrared reflection coefficients, typically greater than 95%.

Advantageously, the reflective surface is coated with a layer of protection against a corrosion of the metallic material.

Thus, the corrosion (such as a sulphidizing) is avoided, so as not to alter the quality of the optical guide formed by the first and second reflective elements.

According to a characteristic, the sensor comprises a reference infrared detector, and said at least one mirror has a surface roughness greater than a threshold from which the infrared light diffused by said at least one mirror may be detected by the reference infrared detector.

Thus, the infrared light diffused by the mirror surface enables to obtain a flow for a reference path; it is thus possible to take advantage of a quality defect of said at least one mirror.

According to a characteristic, the reflective surface is planar.

Advantageously, the reflective surfaces of the first and second reflective elements are parallel.

Thus, the first and second reflective elements form a planar guide. The inventors have also observed that a slight convexity of the reflective surfaces is not prejudicial to correctly image the light source on the infrared detector(s) and obtain good performances of the NDIR sensor. As an example, slightly convex shapes (such as a spherical cap, having a 40-µm height and a 13-mm diameter) for the planar guide result in a maximum 20% decrease of the detected light intensity.

Advantageously, the connecting portion extends transversely between the first and second ends along the normal to the reflective surfaces, to within ±3°.

Further, the inventors have observed that the approximate orthogonality)(±3° of the connecting portion relative to the reflective, planar, and parallel surfaces is not prejudicial to correctly image the light source on the infrared detector(s), and obtain good performances of the NDIR sensor. For example, the decrease of the detected light intensity is typically smaller than 5% for a 3° difference.

According to a characteristic, the optical cavity comprises no lenses.

Preferably, the gas is selected from the group comprising carbon monoxide, carbon dioxide, at least a hydrocarbon, a hydrochlorofluorocarbon, a chlorofluorocarbon, nitrogen monoxide, nitrogen dioxide, sulfur dioxide, ozone.

The present invention also relates to a method of manufacturing a nondispersive infrared sensor to detect a gas, comprising the steps of:
a) forming an optical cavity capable of receiving the gas, and defined by:
   first and second opposite ends, and
   a connecting portion connecting the first and second ends;
b) arranging a light source to emit infrared light in the optical cavity;
c) arranging at least one infrared detector to detect the infrared light;
d) arranging at least one mirror in the optical cavity to guide the infrared light towards at least one infrared detector;
the method being remarkable in that it comprises a step of forming first and second reflective elements respectively extending at the first and second ends of the optical cavity, and having an infrared light reflection coefficient greater than or equal to 75% for any angle of incidence.

Thus, such a method according to the invention enables to increase the optical efficiency of the optical cavity with respect to the state of the art. The mirror(s) enable to conjugate the light source with the infrared detector(s) in the plane of the optical cavity. Now, the inventors have surprisingly observed that it is possible to correctly image the light source on the infrared detector(s) with the additional presence of a waveguide arranged to guide the infrared light across the thickness of the optical cavity, that is, along the transversal dimension of the connecting portion between the first and second ends. Such a waveguide is formed by the first and second reflective elements respectively extending at the first and second ends of the optical cavity, and having an infrared light reflection coefficient greater than or equal to 75% for any angle of incidence.

Advantageously, step a) comprises the steps of:
$a_1$) providing first and second substrates of a material, the material being preferably semiconductor, more preferably silicon;
$a_2$) hollowing each of the first and second substrates so as to form a recessed surface and to keep a surface portion; step $a_2$) being preferably executed by reactive ion etching;
$a_S$) assembling the first and second substrates so that:
   the recessed surfaces form the first and second opposite ends of the optical cavity,
   the surface portions kept at step $a_2$) form the connecting portion connecting the first and second ends.

Thus, the recesses of the first and second substrates obtained at step $a_2$) enable to obtain two half-cavities. The optical cavity is formed at step $a_S$) by assembling the first and second substrates to join the two half-cavities together. The fact of forming a recess, for example, by reactive ion etching, in a substrate of a semiconductor material is a viable low-cost solution since the obtained inclination of the surface portions relative to the normal to the first and second substrates is typically in the range from 1° to 2°. The obtained connecting portion thus extends transversely between the first and second ends of the optical cavity along the normal to the first and second substrates, to within ±3°. It is thus possible to correctly image the light source on the infrared detector(s) and to obtain good performances of the NDIR sensor. For example, the decrease of the detected light intensity is typically smaller than 5% for a 3° difference.

Advantageously, the first and second reflective elements are formed by deposition of a metallic material on the recessed surfaces of the first and second substrates.

Advantageously, said at least one mirror arranged at step d) is formed by the deposition of a metallic material on a lateral edge of a surface portion kept at step $a_2$).

According to a variation, step a) comprises the steps of:
$a_1$) providing first and second molds respectively comprising an impression of first and second parts, each comprising a base topped with a surface portion;
$a_2$) injecting a plastic material into the first and second molds to obtain the first and second parts;
$a_S$) assembling the first and second parts so that:
   the bases form the first and second opposite ends of the optical cavity,
   the surface portions form the connecting portion connecting the first and second ends.

Thus, the optical cavity is formed at step $a_S$) by assembling the first and second parts to join together two half-cavities each defined by the base and the corresponding surface portion. Plastic injection is a viable low-cost solution since shape defects are not prejudicial to correctly image the light source on the infrared detector(s). As an example, slightly convex shapes (such as a spherical cap, having a 40-μm height and a 13-mm diameter) for the planar guide (formed from the bases) result in a maximum 20% decrease of the detected light intensity.

Advantageously, the first and second reflective elements are formed by deposition of a metallic material on the bases of the first and second parts.

Advantageously, said at least one mirror arranged at step d) is formed by deposition of a metallic material on a lateral edge of a surface portion.

BRIEF DESCRIPTION OF THE DRAWINGS

The foregoing and other features and advantages will be discussed in detail in the following non-limiting description of different embodiments of the invention, in connection with the accompanying drawings, among which.

DETAILED DESCRIPTION

Figure 1:
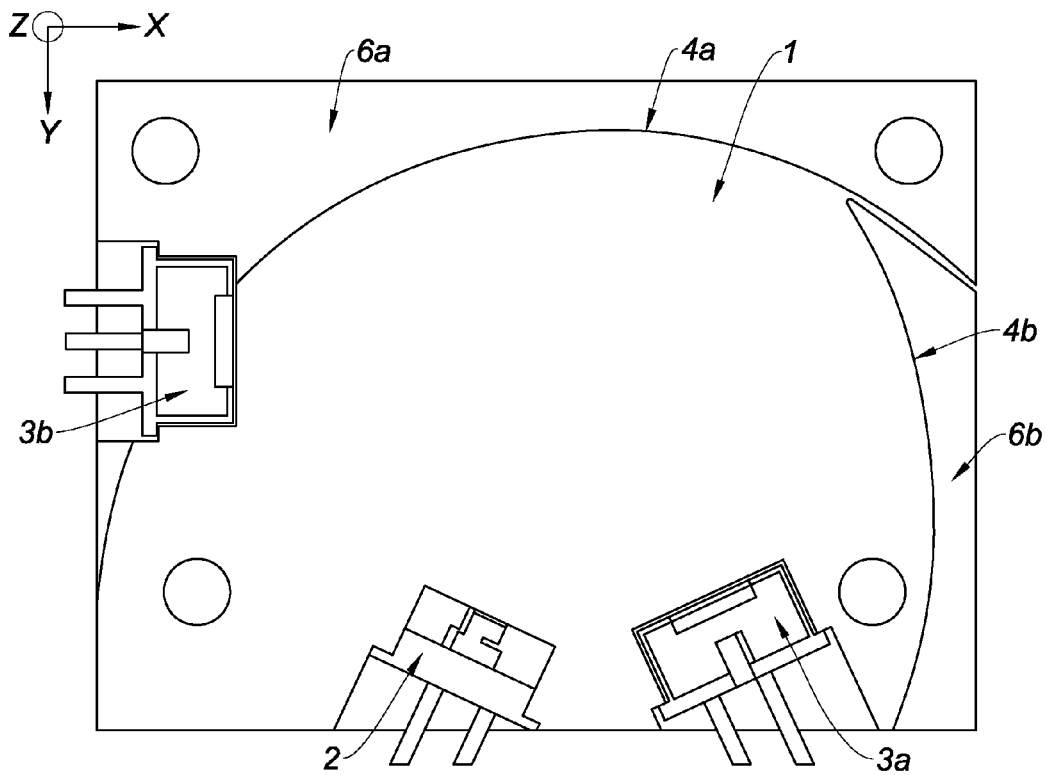
FIG. 1 is a schematic cross-section view of a NDIR sensor according to the invention.
Figure 2:
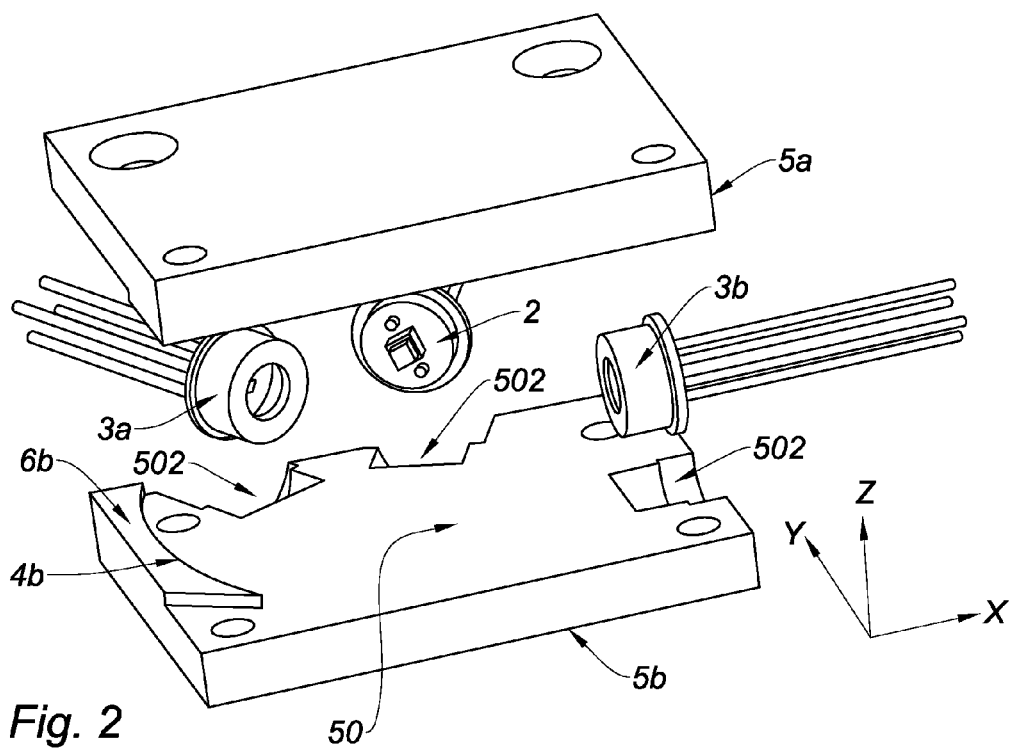
FIG. 2 is a schematic exploded perspective view of a NDIR sensor according to the invention.
Figure 3:
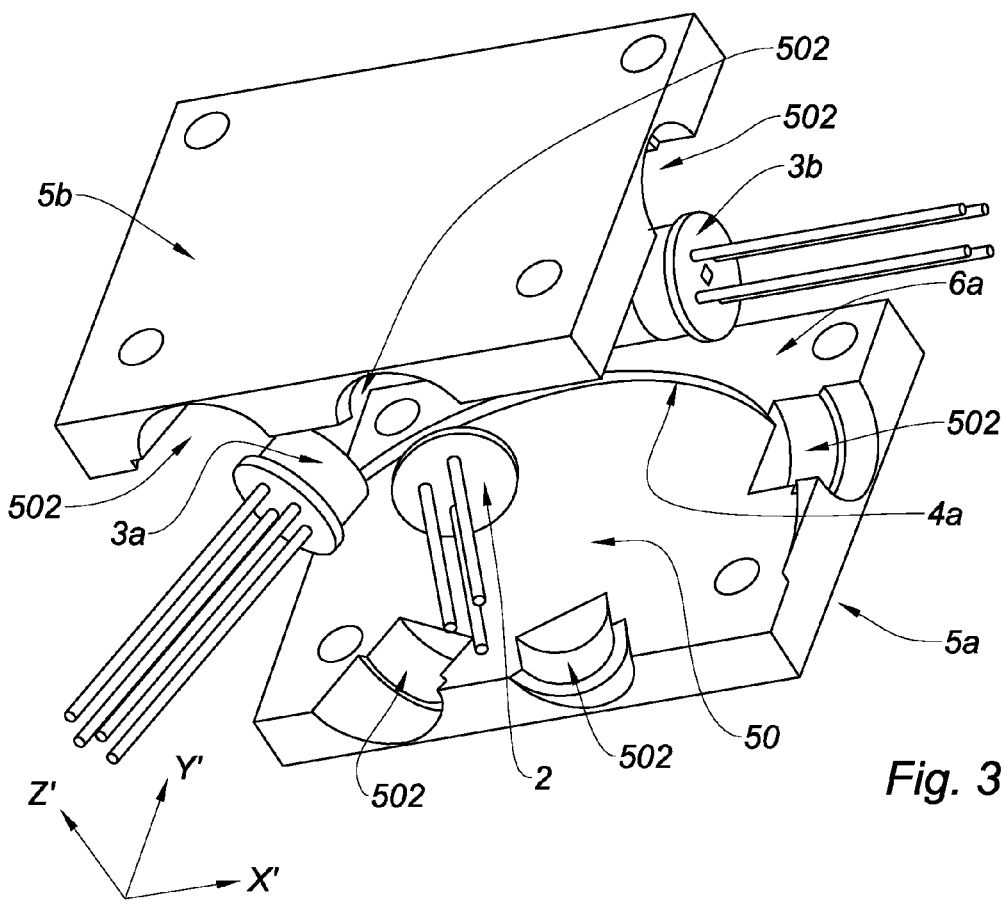
FIG. 3 is a schematic exploded perspective view of the NDIR sensor illustrated in FIG. 2 according to a different viewing angle.

For the different embodiments, the technical characteristics described hereafter are to be considered alone or according to any technically possible combination; the same reference numerals are used for identical elements or elements carrying out the same function, to simplify the description.

FIGS. 1 to 13 illustrate a nondispersive infrared gas detection sensor (NDIR), comprising:
an optical cavity 1 capable of receiving the gas, and defined by:
first and second opposite longitudinal ends 100, 101, and
a connecting portion 6a, 6b extending transversely between first end 100 and second end 101 to connect first and second ends 100, 101;
a light source 2 arranged to emit infrared light in optical cavity 1;
measurement infrared detector 3a and reference infrared detector 3b arranged to detect the infrared light;
elliptical measurement mirror 4a and elliptical reference mirror 4b arranged in optical cavity 1 to guide the infrared light towards said infrared detectors 3a, 3b.

The NDIR sensor comprises first and second reflective elements 5a, 5b respectively extending at the first and second ends 100, 101 of optical cavity 1, and having an infrared light reflection coefficient greater than or equal to 75% for any angle of incidence.

Further, light source 2 is arranged between first end 100 and second end 101. Light source 2 is arranged to be directed towards connecting portion 6a, 6b.

First and Second Reflective Elements

First and second reflective elements 5a, 5b preferably have an infrared light reflection coefficient greater than or equal to 80%, preferably greater than or equal to 85%, more preferably greater than or equal to 90%, for any angle of incidence. Advantageously, the infrared light reflection coefficient is greater than or equal to 95%, preferably greater than or equal to 98%, for any angle of incidence smaller than 45°.

First and second reflective elements 5a, 5b are preferably each formed from a plate. The plates are provided with transversal openings 502 shaped to receive light source 2 and infrared detectors 3a, 3b when the plates are placed into contact and fastened to each other. Each of first and second elements 5a, 5b may comprise a reflective surface 50 having the infrared light reflection coefficient (see above for the quantification). Reflective surface 50 may be curved or textured. Preferably, reflective surface 50 is planar and first and second elements 5a, 5b advantageously form planar mirrors.

Each plate comprises a surface portion 6a, 6b topping reflective surface 50. Reflective surface 50 and surface portion 6a, 6b of each plate define a half-cavity. When the plates are placed into contact and fastened to each other:
reflective surfaces 50 form first and second opposite ends 100, 101 of optical cavity 1,
surface portions 6a, 6b form the connecting portion connecting the first and second ends 100, 101.

In other words, reflective surfaces 50 form the first and second opposite longitudinal ends of optical cavity 1, and surface portions 6a, 6b form transversal walls of the optical cavity connecting first and second ends 100, 101.

Figure 4:
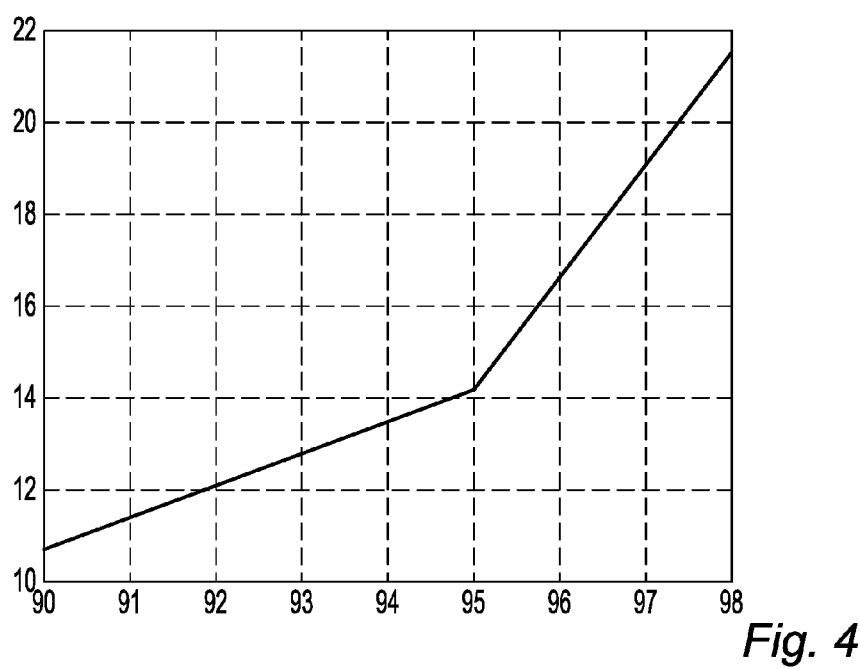
FIG. 4 is a graph showing in abscissas the infrared light reflection coefficient (in %) of the first and second reflective elements, and in ordinates the light flow (in % of the flow emitted by the light source) received on the infrared detector(s)

The variation of the light flow received by infrared detectors 3a, 3b (in % of the flow emitted by light source 2) is illustrated in FIG. 4 for different values of reflection coefficients. It can be observed that the variation of the light flow is not linear according to the reflection coefficient, and that the received light flow increases all the faster as there is a strong reflection coefficient.

Reflective surface 50 of each of the first and second reflective elements 5a, 5b is preferably planar. Reflective surface 50 of each of the first and second reflective elements 5a, 5b is advantageously made of a metallic material, preferably selected from the group comprising gold, silver, and aluminum. Reflective surface 50 of each of first and second reflective elements 5a, 5b is advantageously coated with a layer of protection against a corrosion of the metallic material. The protection layer is advantageously made of a material selected from the group comprising SiO$_2$, SiN, Si$_3$N$_4$, a DLC (Diamond-like carbon) amorphous carbon, polytetrafluoroethylene (PTFE), Pt, TiN. Planar reflective surfaces 50 of first and second reflective elements 5a, 5b are advantageously parallel.

Mirror Assembly

The NDIR sensor advantageously comprises a mirror assembly including elliptical mirrors 4a, 4b arranged to detect the infrared light. The elliptical mirrors 4a, 4b advantageously have an infrared reflection coefficient greater than or equal to 75% for any angle of incidence. Said reflection coefficient is advantageously greater than or equal to 80%, preferably greater than or equal to 85%, more preferably greater than or equal to 90%, for any angle of incidence. Advantageously, the infrared light reflection coefficient is greater than or equal to 95%, preferably greater than or equal to 98%, for any angle of incidence smaller than 45°.

According to an advantageous characteristic, at least one mirror from elliptical mirrors 4a, 4b has a surface roughness greater than a threshold from which the infrared light diffused by the surface of the corresponding mirror 4a or 4b can be detected by the reference infrared detector 3b. The inventors have surprisingly observed that the diffusion of infrared light by the rough surface of the corresponding mirror is not prejudicial to correctly image light source 2 on infrared detectors 3a, 3b, and obtain good performances of the NDIR sensor. It is thus possible to take advantage of a quality defect of the corresponding mirror 4a or 4b to obtain a flow for a reference path, the flow being formed by the infrared light diffused by the rough surface of the corresponding mirror.

According to a variation, at least one mirror from elliptical mirrors 4a, 4b has a texture or waviness adapted so that the infrared light diffused by the waviness can be detected by a reference infrared detector 3b.

For this purpose, the waviness has an averaged period (noted "a") verifying the following relation:

$$a = \lambda \frac{L}{l}$$

where:
L is the characteristic dimension (e.g. the length) of optical cavity 1,
λ is the wavelength of the infrared light,
l is the distance between the corresponding mirror 4a or 4b and reference infrared detector 3b.

Average period "a" is not constant all over the wavy surface to avoid inducing diffraction orders.

The inventors have observed that the diffusion of infrared light by such a wavy surface enables to correctly image light source 2 on infrared detectors 3a, 3b and obtain good performances of the NDIR sensor. It is thus possible to obtain a flow for a reference path, the flow being formed by the infrared light diffused by the wavy surface.

The mirror assembly preferably comprises the elliptical measurement mirror 4a and the elliptical reference mirror 4b. Elliptical measurement mirror 4a is mounted on the plate of first reflective element 5a. More specifically, elliptical measurement mirror 4a is arranged on the reflective surface 50 of first reflective element 5a. Elliptical measurement mirror 4a preferably extends on a lateral edge of surface portion 6a of the plate of first reflective element 5a. Elliptical reference mirror 4b is mounted on the plate of second reflective element 5b. More specifically, elliptical measurement mirror 4b is arranged on the reflective surface 50 of second reflective element 5b. Elliptical reference mirror 4b preferably extends on a lateral edge of surface portion 6b of the plate of second reflective element 5b.

As a non-limiting example, dimensions (a, b, c) of the ellipses of first and second elliptical mirrors 4a, 4b are gathered in the following table:

| Dimension | a (mm) | b (mm) | c (mm) |
|---|---|---|---|
| Measurement mirror 4a | 15 | 14.58 | 3.5 |
| Reference mirror 4b | 18.28 | 17 | 6 | where "a" is the semi major axis, "b" is the semi minor axis, and "c" is the distance between the center and the focus of the corresponding ellipse.

Figure 5:
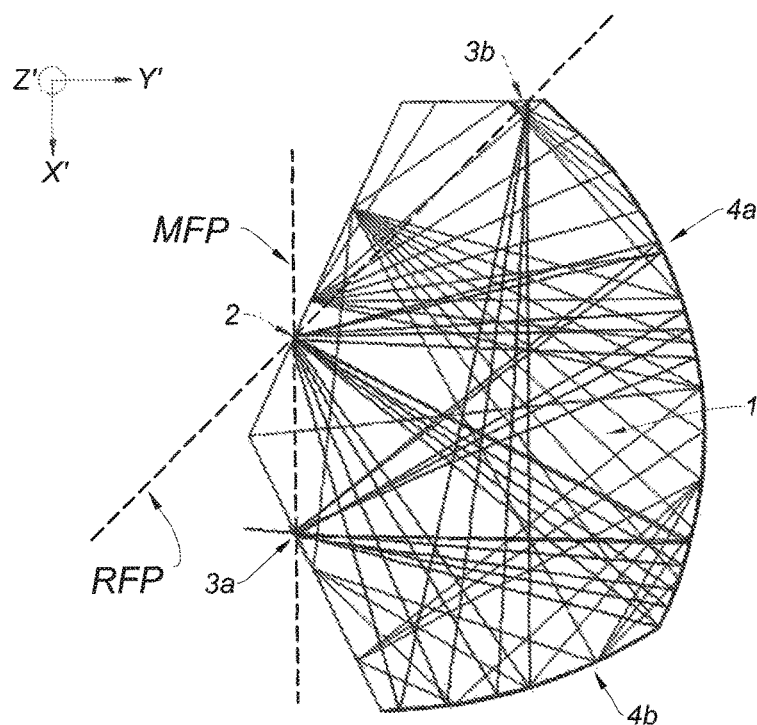
FIG. 5 is a schematic top view illustrating the path of the light beams within the optical cavity for a specific arrangement of mirrors and of infrared detectors.
Figure 6:
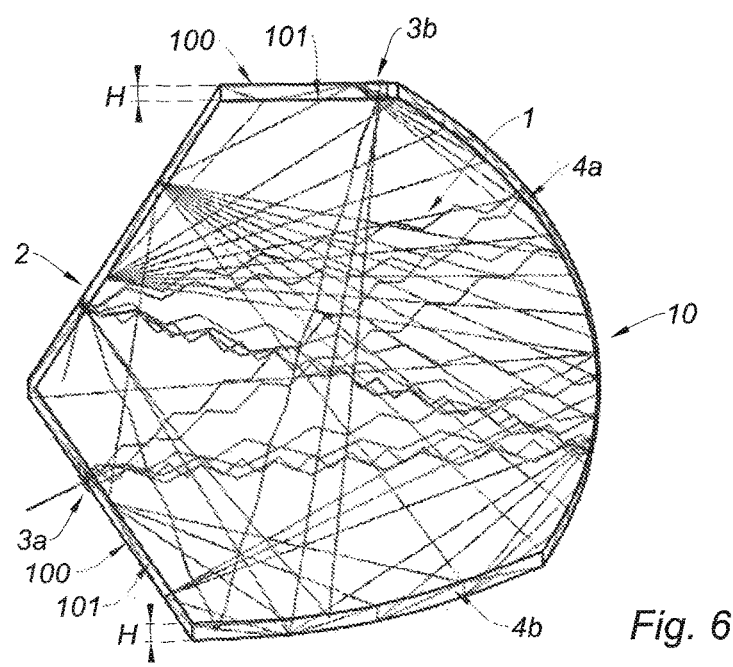
FIG. 6 is a schematic perspective view illustrating the path of the light beams within the optical cavity, for the same specific arrangement as FIG. 5, FIGS. 7 and 8 are schematic side views, respectively, of the first and second reflective elements.

As illustrated in FIGS. 5 and 6, the two focuses of each of the elliptical mirrors 4a, 4b are in planes respectively called measurement focal plane MFP and reference focal plane RFP, extending across the thickness of optical cavity 1 (that is, along Z or Z'). As a non-limiting example, the MFP and RFP planes form together a 45° dihedron angle.

The mirror assembly may have different configurations according to the interaction length l desired between the gas and the infrared light and the number of infrared detectors used.

According to a first variation, it is possible to suppress an elliptical mirror if a single infrared detector, e.g., 3a or 3b, is used, and this, to maximize the received flow for an application requiring a high sensitivity.

According to a second variation, it is possible to partition an elliptical mirror into a plurality of portions of elliptical mirrors having a common focus if a plurality of infrared detectors, e.g., 3a and 3b, are used.

Figure 11:
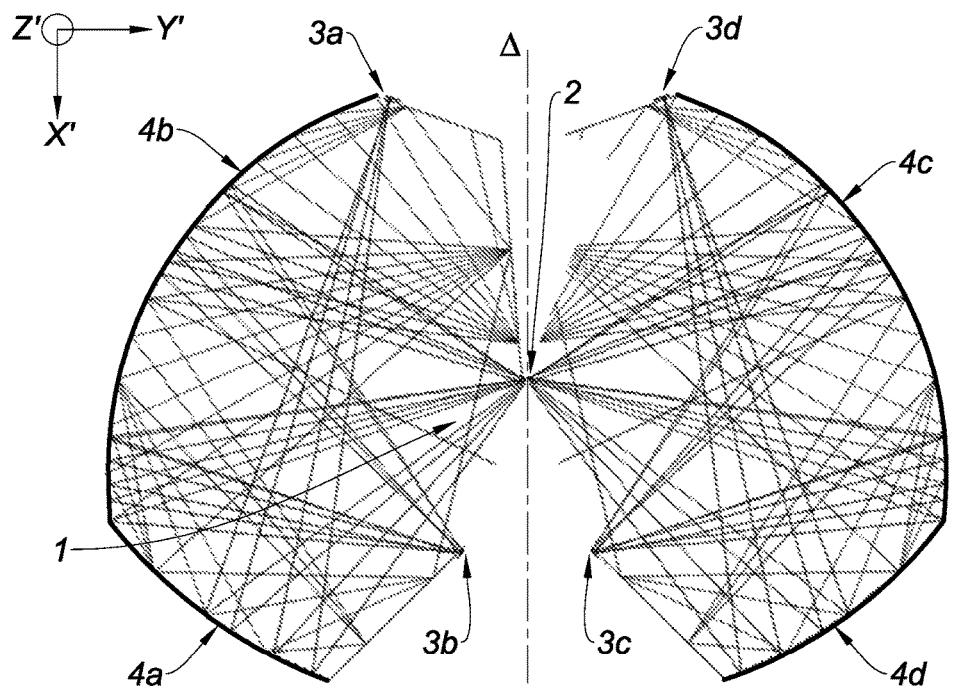
FIGS. 11 to 13 are schematic top views illustrating the path of the light beams within the optical cavity for different arrangements of mirrors and of infrared detectors.

According to a third variation illustrated in FIG. 11, it is possible to symmetrically arrange an assembly of elliptical mirrors 4a, 4b, 4c, 4d in plane (X', Y') of optical cavity 1 on either side of an axis of symmetry Δ, and to arrange a light source 2 along axis of symmetry Δ to optimize the electric power consumption of light source 2, light source 2 emitting in all directions. Infrared detectors 3c and 3d are positioned symmetrically with respect to infrared detectors 3b and 3a.

Figure 12:
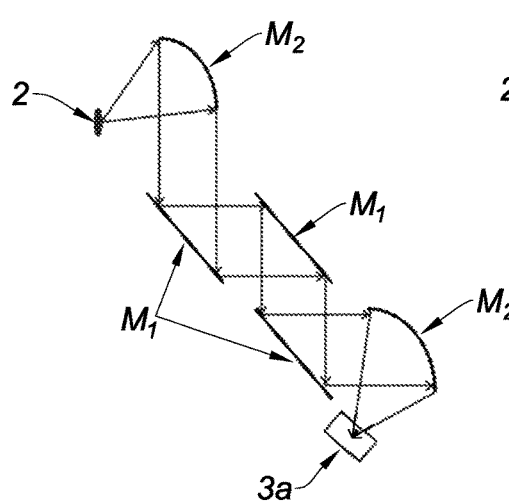
Figure 13:
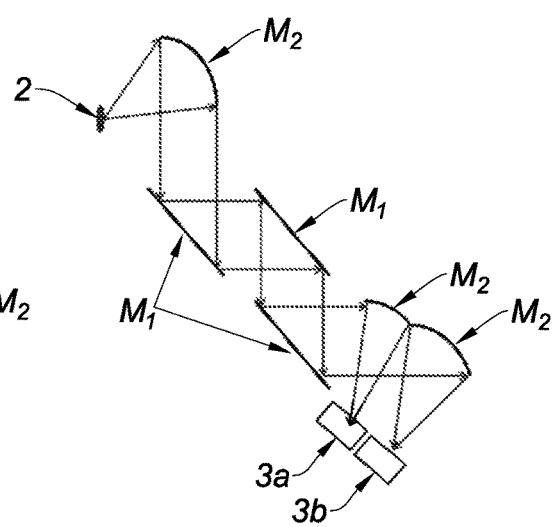

According to a fourth variation illustrated in FIGS. 12 and 13, it is possible to replace elliptical mirrors 4a, 4b with off-axis parabolic mirrors $M_2$ (that is, off the optical axis) and planar mirrors $M_1$. A parabolic mirror $M_2$ is arranged to collimate light source 2; the collimated beam is reflected by planar mirrors $M_1$ and is then focused on measurement infrared detector 3a (FIG. 12) or measurement infrared detector 3a and reference infrared detector 3b (FIG. 13) by at least one additional parabolic mirror $M_2$.

Optical Cavity

Preferably, elliptical measurement mirror 4a, elliptical reference mirror 4b, and reflective surfaces 50 of the first and second reflective elements 5a, 5b form a cylinder 10 defining optical cavity 1.

The directrix curve of cylinder 10, corresponding to a cross-section of cylinder 10 in a plane (X, Y)- or (X', Y')-, is an open curve comprising first and second elliptical portions (see FIG. 1). The first and second elliptical portions correspond to elliptical measurement mirror 4a and elliptical reference mirror 4b. First and second ends 100, 101 of cylinder 10 (that is, the bases of cylinder 10) are preferably closed by reflective surfaces 50 of first and second reflective elements 5a, 5b. The thickness of optical cavity 1 corresponds to height H of cylinder 10, along direction Z (or Z'). As an example, H=600 μm.

Other shapes may be envisaged for optical cavity 1. Reflective surfaces 50 form first and second ends 100, 101 of optical cavity 1. Reflective surfaces 50 and connecting portion 6a, 6b (possibly mirror(s) 4a, 4b extending from connecting portion 6a, 6b) define optical cavity 1.

As non-limiting examples, connecting portions 6a, 6b may extend transversely between reflective surfaces 50 along a direction which is curvilinear (and thus nonrectilinear, conversely to cylinder 10). The curvilinear direction may form an arc of a circle, in which case reflective surfaces 50 and connecting portion 6a, 6b may form a torus truncated by a plane perpendicular to the curvilinear direction. The truncated torus may comprise openings capable of receiving light source 2 and infrared detectors 3a, 3b. "Torus" designates the surface generated by the revolution of a planar curve (open or curved) around an axis located in the plane of said planar curve.

Reflective surfaces 50 and connecting portion 6a, 6b may form a frustum with parallel bases, reflective surfaces 50 forming the parallel bases. The frustum may comprise openings capable of receiving light source 2 and infrared detectors 3a, 3b.

Optical cavity 1 advantageously comprises no lenses.

Light Source

Light source 2 preferably comprises an infrared radiation emission element. Light source facing connecting portion 6a, 6b means that said emitter element is arranged opposite connecting portion 6a, 6b. Preferably, the optical axis of light source 2 is directed towards connecting portion 6a, 6b.

Light source 2 advantageously comprises an emitter element, for example, of filament type, which is made to conduct an electric current so that the element heats up and emits an infrared radiation. The element has a dimension h along direction Z (or Z') and preferably verifies:

100 μm ≤ h ≤ H ≤ 1.5 mm, preferably 250 μm ≤ h ≤ H ≤ 1200 μm.

The element preferably has the shape of a disk with a circular surface, having a 250-μm diameter (corresponding to dimension h).

The axis of light source 2, or the optical axis of light source 2, is defined as the normal to the circular surface. As a non-limiting example, the disk may have a 400-nm thickness along the axis of light source 2. The directrix curve of cylinder 10 images light source 2 in a single direction, that is, the plane of optical cavity 1. The image of light source 2 (that is, the disk-shaped element) is a rectangle having a 250-μm width and a 600-μm height (corresponding to the height of optical cavity 1). Preferably, the normal to said rectangle (image of light source 2) is directed towards connecting portion 6a, 6b. More preferably, the normal is interposed between first and second ends 100, 101, and it is substantially parallel to said ends 100, 101.

Infrared Detectors

The NDIR sensor preferably comprises two infrared detectors: a measurement infrared detector 3a, and a reference infrared detector 3b. Measurement infrared detector 3a and reference infrared detector 3b are respectively in the MFP plane and in the RFP plane. Each infrared detector 3 has a surface preferably sensitive to infrared, arranged between first end 100 and second end 101, and arranged opposite connecting portion 6a, 6b.

As a non-limiting example, the sensitive surface may have the shape of a square having a 600-µm side length. The axis of the infrared detectors 3a, 3b is defined as the normal to the sensitive surface. The axis of light source 2 and axis X (or X') preferably form a 25° angle to maximize the light flow received by infrared detectors 3a, 3b. In other words, the axis of light source 2 preferably forms a 25° angle with the MFP. The axis of measurement infrared detector 3a and axis X (or X') preferably form a 25° angle to optimize the received light flow. In other words, the axis of measurement infrared detector 3a preferably forms a 25° angle with the MFP. The axis of reference infrared detector 3b is preferably perpendicular to axis Y (or Y') to optimize the received light flow. The axis of reference infrared detector 3b preferably forms a 45° angle with the RFP.

Measurement infrared detector 3a is preferably equipped with an optical filter of bandpass type, centered on the spectral absorption band of the gas to be detected. As non-limiting examples, the gas is selected from the group comprising carbon monoxide, carbon dioxide, at least a hydrocarbon, a hydrochlorofluorocarbon, a chlorofluorocarbon, nitrogen monoxide, nitrogen dioxide, sulfur dioxide, ozone. Reference infrared detector 3b is preferably equipped with an optical filter centered on a spectral band which is absorbed by no gas to be detected.

As non-limiting examples, the gas may also be selected from the following gases, which absorb in a spectral absorption band in the range from 0.78 µm to 12 µm:
HF, HCl, $SO_3$, HBr, $H_2S$, COS, $C_2H_6$, $C_3H_8$, $C_4H_{10}$, $COCl_2$, $BF_3$, $CH_4$, $HNO_3$, a volatile organic compound (e.g. $C_6H_6$, $CH_3COCH_3$), $B_2H_6$, CO, $CS_2$, HCN, $WF_6$, $N_2O$, $NH_3$,
$AsH_3$, a polycyclic aromatic hydrocarbon, benzene, toluene, the three isomers of xylene, $C_2H_4O$, $BCl_3$.

The spectral transmission band of conventional filters generally depends on the angle of incidence. In other words, for angles greater than a given threshold (for example, 45° or also 30°), the filter transmits wavelengths which are no longer in the absorption band of the gas to be detected.

Thus, such a NDIR sensor according to the invention enables to increase, at the same time, the optical efficiency and the compactness of the optical cavity with respect to the state of the art, while optimizing the angular distribution of the infrared radiation collected by the detector(s). The ingenious arrangement of the different sensor elements, particularly, the light source, the infrared detector(s), the mirror(s), and the reflective elements extending at the ends of the optical cavity, enables to conjugate the light source with the infrared detector(s) in the plane of the optical cavity, to guide the infrared light across the thickness and according to an optimal angular distribution (angles of incidence smaller than said threshold for a majority of the incident radiations) to use at best the angular emission properties of the light source.

Manufacturing Method

A method of manufacturing a nondispersive infrared sensor to detect a gas, comprises the steps of:
a) forming an optical cavity 1 capable of receiving the gas, and defined by:
  first and second opposite ends 100, 101, and
  a connecting portion 6a, 6b connecting the first and second ends 100, 101;
b) arranging a light source 2 to emit infrared light in optical cavity 1;
c) arranging infrared detectors 3a, 3b to detect the infrared light;
d) arranging elliptical mirrors 4a, 4b in optical cavity 1 to guide the infrared light towards said infrared detectors 3a, 3b.

The method comprises a step of forming first and second reflective elements 5a, 5b respectively extending at the first and second ends 100, 101 of optical cavity 1, and having an infrared light reflection coefficient greater than or equal to 75% for any angle of incidence.

Figure 7:
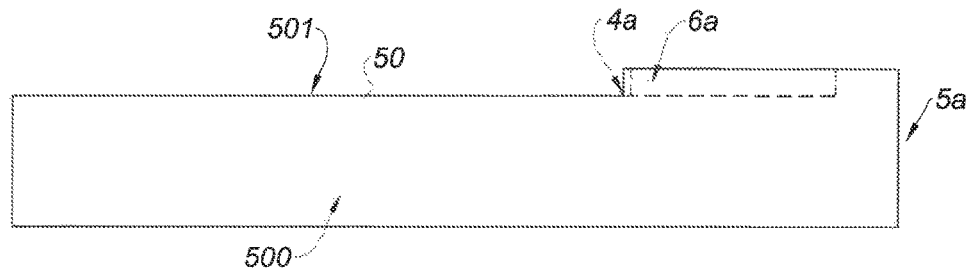
Figure 8:
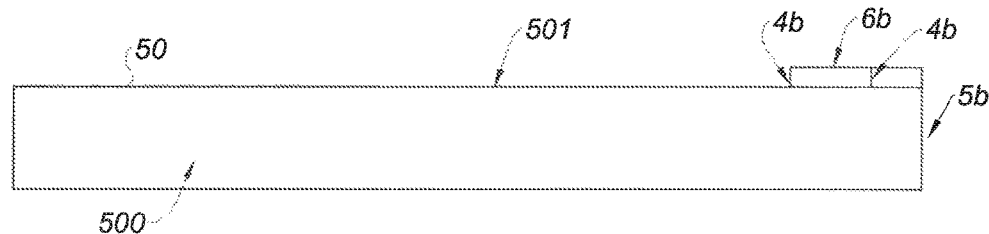
Figure 9:
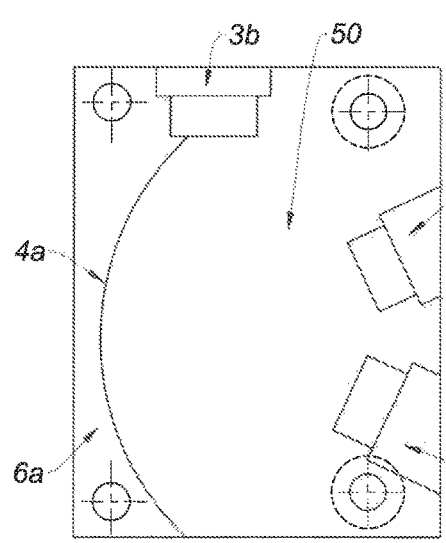
FIGS. 9 and 10 are schematic top views, respectively, of the first and second reflective elements.
Figure 10:
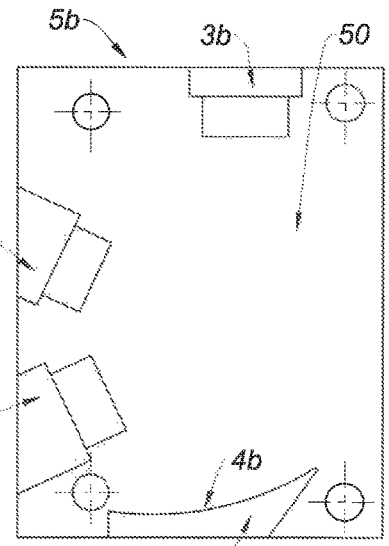

According to a first embodiment illustrated in FIGS. 7 and 8, step a) comprises the steps of:
$a_1$) providing first and second substrates 500 of a material, the material being preferably semiconductor, more preferably silicon;
$a_2$) hollowing each of the first and second substrates 500 so as to form the reflective surface 50 as a recessed surface and to keep a surface portion 6a, 6b,
$a_S$) assembling the first and second substrates 500 so that:
  reflective surfaces 50 form first and second opposite ends 100, 101 of optical cavity 1,
  surface portions 6a, 6b kept at step $a_2$) form the connecting portion connecting the first and second ends 100, 101.

Step $a_2$) is advantageously executed by deep reactive ion etching. Step $a_2$) preferably comprises a previous step comprising depositing a resist at the surface of first and second substrates 500. Then, recesses 501 may be obtained by photolithography and etch steps. Step $a_2$) is advantageously executed so that the obtained recesses 501 enable to form planar reflective surfaces 50.

First and second reflective elements 5a, 5b are advantageously formed by deposition of a metallic material on reflective surfaces 50 of first and second substrates 500, the deposition being preferably executed by cathode sputtering. The deposition of the metallic material may also be executed by vacuum evaporation or by electrolysis. The deposition of the metallic material is executed before step $a_S$).

Elliptical mirrors 4a, 4b are advantageously formed by deposition of a metallic material on a lateral edge of a surface portion 6a, 6b, the deposition being preferably executed by cathode sputtering. The deposition of the metallic material may also be executed by vacuum evaporation or by electrolysis. The deposition of the metallic material is executed before step $a_S$).

According to a second embodiment, step a) comprises the steps of:
$a_1$) providing first and second molds respectively comprising an impression of first and second parts, each comprising a substrate 500 as a base topped with a surface portion 6a, 6b;
$a_2$) injecting a plastic material into the first and second molds to obtain the first and second parts,
$a_S$) assembling the first and second parts so that:
  substrates 500 form first and second opposite ends 100, 101 of optical cavity 1,
  surface portions 6a, 6b form the connecting portion connecting first and second ends 100, 101.

Step $a_1$) is preferably executed so that the first and second molds each comprise a fixed portion and a mobile portion. Step $a_2$) is preferably executed with an injection press.

First and second reflective elements 5a, 5b are advantageously formed by deposition of a metallic material on substrates 500 of the first and second parts, the deposition being preferably executed by cathode sputtering. The deposition of the metallic material may also be executed by vacuum evaporation or by electrolysis. The deposition of the metallic material is executed before step $a_S$).

Elliptical mirrors 4a, 4b are advantageously formed by deposition of a metallic material on a lateral edge of a surface portion 6a, 6b, the deposition being preferably executed by cathode sputtering. The deposition of the metallic material may also be executed by vacuum evaporation or by electrolysis. The deposition of the metallic material is executed before step as).

The invention claimed is:

1. A nondispersive infrared gas detection sensor comprising:
   a first planar mirror;
   and a second planar mirror;
   a connecting portion disposed between the first planar mirror and the second planar mirror and connecting the first planar mirror with the second planar mirror, the connecting portion and the first and second planar mirrors defining an optical cavity designed to receive a gas;
   a light source arranged to emit an infrared light in the optical cavity, the light source being located between a first plane defined by the first planar mirror and a second plane defined by the second planar mirror;
   at least one infrared detector arranged to detect the infrared light, the at least one infrared detector being located between the first plane and the second plane;
   at least one additional mirror arranged in the optical cavity to guide the infrared light towards the at least one infrared detector,
   wherein the first and second planar mirrors have completely flat surfaces and an infrared light reflection coefficient greater than or equal to 75% for any angle of incidence of the infrared light with the first and second planar mirrors, and
   the light source is arranged between the first and second planar mirrors and oriented to emit the infrared light on the first planar mirror.

2. The sensor of claim 1, wherein the connecting portion defines a curvilinear sidewall in a section plan perpendicular to the first and second planar mirrors.

3. The sensor of claim 2, wherein the curvilinear sidewall defines an arc of a circle in a section plan perpendicular to the first and second planar mirrors, and
   the first and second planar mirrors and the connecting portion form a truncated torus defining the optical cavity, the torus being truncated by a plane perpendicular to the curvilinear direction.

4. The sensor of claim 1, wherein the first and second planar mirrors and the connecting portion form a frustum with parallel bases defining the optical cavity, the first and second planar mirrors forming the parallel bases.

5. The sensor of claim 1, wherein each of the first and second planar mirrors is coated with a layer of protection against a corrosion of the metallic material, the layer of protection being made of a material selected from the group consisting of $SiO_2$, SiN, $Si_3N_4$, a Diamond-like Carbon type amorphous carbon, polytetrafluoroethylene, Pt and TiN.

6. The sensor of claim 1, wherein the at least one infrared detector comprises a reference infrared detector and a measurement infrared detector, the at least one additional mirror arranged in the optical cavity guiding the infrared light towards the measurement infrared detector and the at least one additional mirror has a surface roughness diffusing a part of the infrared light, the diffused infrared light being detected by the reference infrared detector.

7. The sensor of claim 1, wherein the first and second planar mirrors are parallel.

8. The sensor of claim 7, wherein the connecting portion extends transversely between the first and second ends along the normal to the reflective surfaces to within ±3°.

9. The sensor of claim 1, wherein the at least one additional mirror connects the first planar mirror with the second planar mirror.

10. The sensor of claim 1, wherein the at least one additional mirror comprises first and second elliptical mirrors each defined by an ellipse having a semi major axis, a semi minor axis and a distance separating a center of the ellipse with two focuses of the ellipse, the two focuses of the first elliptical mirror define a first axis and the two focuses of the second elliptical mirror define a second axis and wherein the light source is arranged on the first axis and the at least one infrared detector is arranged on the second axis.

11. The sensor of claim 10, wherein the first axis cuts the second axis with an angle equal to 45°.

12. A method of manufacturing a nondispersive infrared sensor to detect a gas, the method comprising the steps of:
   a) forming an optical cavity designed to receive the gas, and defined by a connecting portion disposed between a first planar mirror and a second planar mirror that connects the first planar mirror with the second planar mirror;
   b) arranging a light source to emit infrared light in the optical cavity, the light source being located between a first plane defined by the first planar mirror and a second plane defined by the second planar mirror;
   c) arranging at least one infrared detector to detect the infrared light, the at least one infrared detector being located between the first plane and the second plane;
   d) arranging at least one additional mirror in the optical cavity to guide the infrared light towards the at least one infrared detector,
   wherein the first and second planar mirrors have completely flat surfaces and an infrared light reflection coefficient greater than or equal to 75% for any angle of incidence of the infrared light with the first and second planar mirrors, and
   the light source is arranged between the first and second planar mirrors and oriented to emit the infrared light on the first planar mirror.

13. The method of claim 12, wherein step a) comprises the steps of:
   $a_1$) providing first and second substrates of a material;
   $a_2$) hollowing each of the first and second substrates so as to form a recessed surface and to keep a surface portion; and
   $a_3$) assembling the first and second substrates so that:
      the recessed surfaces form first and second opposite ends of optical cavity, and
      the surface portions kept at step $a_2$) form the connecting portion connecting the first and second ends.

14. The method of claim 13, wherein the first and second reflective elements are formed by deposition of a metallic material on the recessed surfaces of the first and second substrates.

15. The method of claim 13, wherein the at least one mirror arranged at step d) is formed by deposition of a metallic material on a lateral edge of a surface portion kept at step $a_2$).

16. The method of claim 12, wherein step a) comprises the steps of:
   $a_1$) providing first and second molds respectively comprising an impression of first and second parts each comprising a base topped with a surface portion;
   $a_2$) injecting a plastic material into the first and second molds to obtain the first and second parts; and a₃) assembling the first and second parts so that:
   the bases form first and second opposite ends of the optical cavity,
   the surface portions form the connecting portion connecting the first and second ends.

17. The method of claim 16, wherein the first and second reflective elements are formed by deposition of a metallic material on the bases of the first and second parts.

18. The method of claim 16, wherein the at least one mirror arranged at step d) is formed by deposition of a metallic material on a lateral edge of a surface portion.

\* \* \* \* \*